United States Patent [19]
Silberklang et al.

[11] Patent Number: 5,486,700
[45] Date of Patent: Jan. 23, 1996

[54] PROXIMITY CONTROLS FOR GAMMA CAMERA

[75] Inventors: Alex Silberklang, Haifa; Israel Ohana, Kiryat Tivon, both of Israel

[73] Assignee: Elscint Ltd., Haifa, Israel

[21] Appl. No.: 172,728

[22] Filed: Dec. 27, 1993

[30] Foreign Application Priority Data

Dec. 31, 1992 [IL] Israel ........................................ 104292

[51] Int. Cl.⁶ .................................................... G01T 1/166
[52] U.S. Cl. .................................. 250/363.04; 250/363.02
[58] Field of Search ......................... 250/363.02, 363.04, 250/363.05, 363.08, 491.1, 221

[56] References Cited

U.S. PATENT DOCUMENTS

| | | | |
|---|---|---|---|
| 3,805,061 | 4/1974 | De Missimy et al. | 250/350 |
| 3,970,846 | 7/1976 | Schofield, Jr. et al. | 250/221 |
| 4,445,035 | 4/1984 | Ueyama | 250/363.04 |
| 4,593,189 | 6/1986 | Stoub | 250/221 |
| 4,818,866 | 4/1989 | Weber | 250/222.1 |
| 5,027,221 | 6/1991 | Hisatake et al. | |
| 5,072,121 | 12/1991 | Jazbec | 250/363.04 |
| 5,319,205 | 6/1994 | Kline et al. | 250/363.04 |

*Primary Examiner*—Carolyn E. Fields
*Attorney, Agent, or Firm*—Sandler, Greenblum & Bernstein

[57] ABSTRACT

Proximity controls for controlling the proximity of a gamma camera to a patient during a scan of the patient. The proximity controls consist of two spaced apart energy screens, each comprising 200 beams, parallel to and spaced from the detector of the gamma camera. When neither screen is interrupted, the camera is moved towards the patient. When both screens are interrupted, the camera is moved away from the patient. When only the screen farthest from the detector is interrupted, the camera is braked so as not to move away from or towards the patient.

22 Claims, 4 Drawing Sheets

PROXIMITY CONTROLS FOR GAMMA CAMERA

FIELD OF THE INVENTION

This invention relates to body scanning apparatus and more particularly, to gamma cameras used to scan patients either in a full body planar scanning mode or in an emission computerized tomographic (ECT or SPECT) scanning mode.

BACKGROUND OF THE INVENTION

During a planar scan of a patient with a gamma camera, the gamma camera travels over the patient parallel to the cranium-caudal axis. During ECT scans the gamma camera rotates around the region of the patient to be imaged. The rotation is in a plane generally orthogonal to the cranial caudal axis of the patient and results in the imaging of a cross sectional slice of the patient's body. In either type of scan, it is important that the camera head be maintained as closely as possible to the patient because this results in better resolution and consequently image quality is improved.

In the prior art especially for ECT studies, it is known to use various methods and systems for maintaining the camera head as closely as possible to the patient. For example, U.S. Pat. No. 4,503,331 provides a non-circular ECT scan path. The scanning path is elliptical and accordingly, it more closely follows the body contour than does a circular path.

In U.S. Pat. No. 4,593,189 a camera head is provided with an optical proximity detector to uric the head towards the patient while rotating around the patient. When the head gets too close to the patient, proximity detector is triggered and the head is moved away from the patient.

U.S. Pat. No. 5,072,121 features an arrangement for determining the planar contour of an object using a plurality of light emitters and detectors positioned in a circular planar array. The array surrounds the object for determining the planar contour of the object, such as the patient. The light emitters are sequentially energized and resulting signals from the light detectors are used for determining the object's planar contour. The camera is then directed on a path emulating the contour.

Each of the above patented systems is an improvement over the original circular path used by gamma cameras during ECT scans. Thus, the patent covering the elliptical orbit improves over the circular orbit, but is merely an approximation of the exact contour of the patient's body. Therefore, the distance of the camera head to the patient can be significantly decreased. The proximity detector, among other things, makes it difficult to change collimators in the camera head to which it is attached. The contour determining arrangement of U.S. Pat. No. 5,072,121 requires a learning cycle wherein the system learns the contour of the body. This requires additional time and, therefore, reduces throughput.

It is, therefore, an object of the present invention to provide systems which speed up the scan procedure by automatically positioning the scanning camera as close as possible to the patient's body, even closer than attainable with a prior art elliptical scan, during the scan regimen without necessitating a learning cycle and without endangering the patient.

BRIEF DESCRIPTION OF THE INVENTION

In accordance with a preferred aspect of the present invention, a gamma camera system is provided, said system comprising:

a gamma camera gentry, means for mounting at least one gamma camera on said gentry for use in performing whole body scans or emission computerized tomographic scans of a patient, said camera having a radiation detecting side, controls for maintaining the distance between the camera and the patient at a minimum, said controls comprising:

a first series of energy transmitters for transmitting energy to which the patient is opaque, said first series of energy transmitters each mounted to said camera at a first distance from the radiation detecting side of said camera toward said patient, a first series of energy receivers each mounted to said camera oppositely disposed from said first series of said energy transmitters at said first distance away from the radiation detecting side of said camera toward said patient so that energy transmitted from said first series of energy transmitters impinge on said first series of energy receivers after spanning the detecting side of the camera, an in-out motor for selectively moving said camera away from or toward the patient, means for operating said motor responsive to the body contour of the patient interrupting the transmitted energy so as to prevent the receipt of the transmitted energy by the first series of receivers to move said camera away from said patient, a second series of energy transmitters each mounted a second distance away from the radiation detecting side of the camera toward said patient, a second series of energy receivers each mounted oppositely disposed from said second series of energy transmitters and at said second distance away from-said radiation detecting side of said camera toward said patient so that energy transmitted from said second series of energy transmitters impinge on said second series of energy receivers after spanning the detecting side of the camera, said second distance being larger than said first distance, means for inhibiting the operation of said in-out motor responsive to interruption of the energy extending from said second series of energy transmitters to the second series of energy receivers whereby the camera does not move in the in or out directions, and means for operating said in-out motor to move said camera toward said patient when there is no interruption with the energy extending from the energy transmitters to the energy receivers.

The gamma camera system of the invention includes means for enabling the control of the in-out motor responsive to energy spanning said radiation detecting side of said camera in two parallel planes, whereby when there is no interruption with the energy in either of the two planes the in-out motor moves the camera toward the patient. When the patient's body interrupts the energy in the plane furtherest from the radiation detecting side of the camera, the in-out motor is de-energized. When the patient's body interrupts both energy planes, the in-out motor is energized to move the camera away from the patient.

According to a feature of the invention, the energy planes are provided by direct transmittal and receipt of the energy at the planes parallel to the detecting side of the gamma camera.

According to an alternative feature of the invention, the energy transmitters and/or receivers could be removed from the parallel planes by the use of reflecting surfaces.

Another feature of the system is a fail-safe provision for causing the in-out motor to move the camera away from the patient responsive to actuation of a pressure sensitive detector.

Still another feature of the invention provides for a dual camera system with each of the cameras having an individual motor for moving the camera radially irrespective of the radial motion of the other camera.

The gamma camera arrangement of the invention provides for maintaining said gamma camera at a distance from the patient wherein said energy extending between said second set of transmitters and said second set of receivers is interrupted and wherein the energy extending from said first set of transmitters to said first set of receivers is not interrupted.

Another feature of the invention provides means for preventing energy cross-talk; i.e., energy transmitted from being received by a receiver that is not coupled to the transmitting transmitter.

Yet another feature of the invention provides a leading set of oppositely disposed energy transmitters and receivers mounted to the gamma camera so as to be responsive to longitudinal motion between the patient and the camera when the patient is being positioned within the viewing range of the camera.

The above named and other objects, features and advantages of the present Invention will be more apparent from the following description of a preferred embodiment of the present invention when considered along with the accompanying drawings; wherein.

BRIEF DESCRIPTION OF THE DRAWINGS

FIG. 2 is a front view of the inventive system of FIG. 1;

FIG. 3 is an enlarged front view of one of the gamma cameras shown in FIGS. 1 and 2;

FIG. 6a and 6b are schematic showings of:

a) the direct generation of the energy planes, and b) the generation of the-energy planes using reflective surfaces.

GENERAL DESCRIPTION OF THE INVENTION

Figure 1:
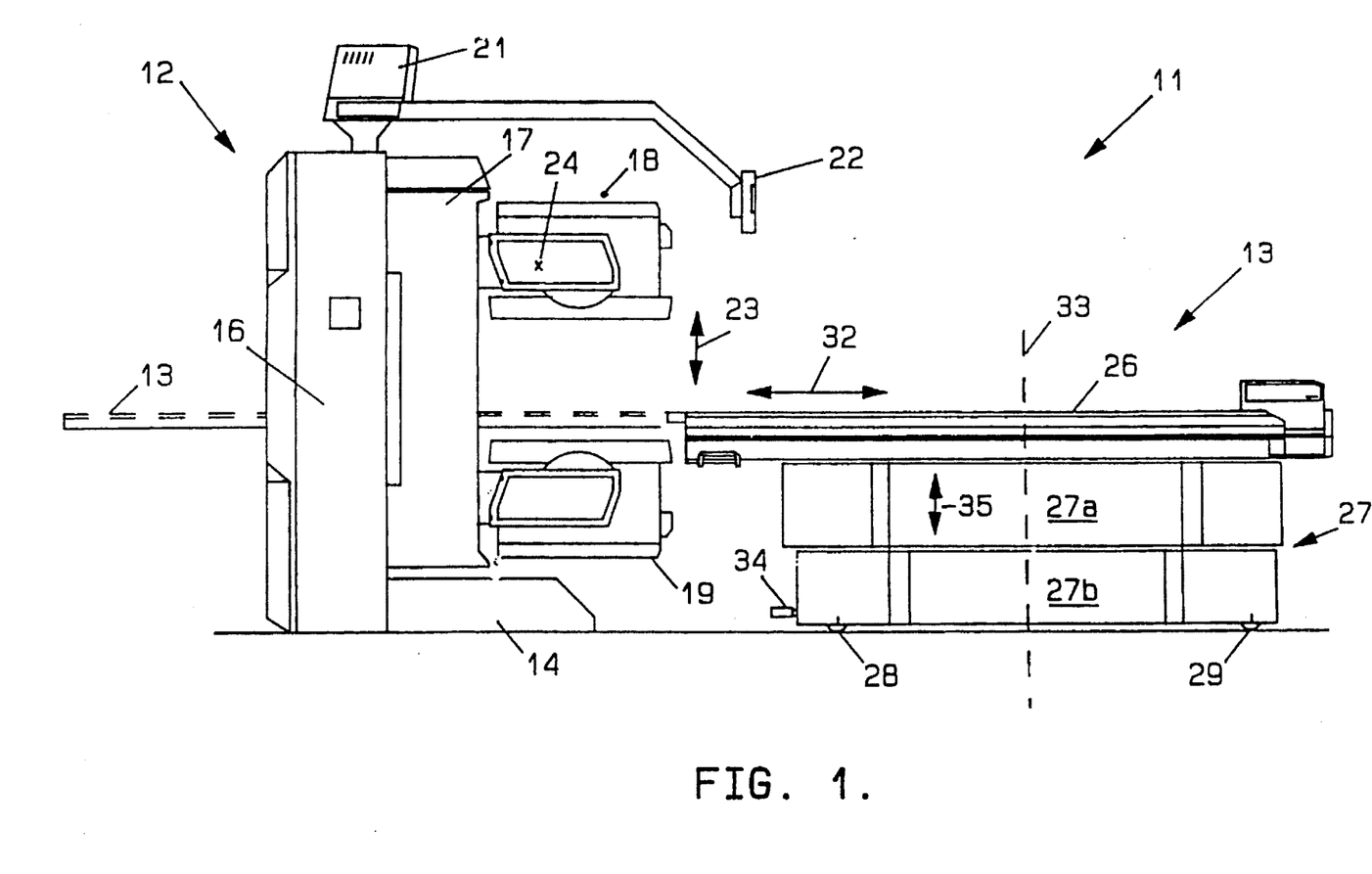
FIG. 1 is a side view of the inventive gamma camera system for maintaining the camera proximate to the patient during scans.

FIG. 1, shows the inventive gamma camera system 11 as a dual gamma camera system which can provide either full body scans or ECT scans. While dual camera heads are shown and the control of a single camera is described herein, it should be understood that the invention also applies to maintaining a single gamma camera or multiple cameras proximate to the patient during scans. The gamma camera system 11 of FIG. 1 comprises a gantry assembly 12 and a patient bed assembly 13. The gantry assembly 12 comprises a base 14, a stator 16 and a rotor 17. The rotor rotates in a circular fashion on the stator 16. Attached to the rotor 17 are two gamma camera heads 18 and 19. With the rotation of the rotor, the heads rotate around the body and provide data for a tomographic image.

Auxiliary to the gantry is a monitor 21 and a remote control unit 22. The remote control unit is used for controlling the movement of the camera heads 18 and 19 which in addition to rotating with the rotor can move up or down as indicated by arrow 23 or can pivot around the pivot point 24 shown in camera 18. A similar Point not shown is associated with camera 19.

The patient bed assembly 13 comprises a patient bed 26 on a base 27. The base is shown as being mounted on casters 28 and 29. During the scanning procedure the base is locked in place and the bed 26 is longitudinally movable as shown by the dashed lines 31 so that during the scan the bed can be moved longitudinally back or forth as shown by arrow 32. When the bed is moved and the rotor remains stationary, then a whole body scan is obtained. When the bed is moved so that the patient's thorax, for example, is beneath the camera, then the SPECT image is acquired in the thorax region of the patient. Alternatively, a helical scan is possible by rotating the rotor while the bed is moving longitudinally relative to the cameras. It should be understood that while longitudinal movement of the bed is described, longitudinal movement of the gantry would provide the same results. It is the relative movement between the bed (i.e., patient) and the gantry that is material.

The remote control unit 22 also controls the movement of the bed 26. The bed 26 can move up or down as indicated by arrow 25, when upper base section 27a moves up or down on lower base section 27b. In addition, the bed can swivel around axis 33 when a swivel lock lever 34 is pressed to release the lock. The swivelling of the bed makes it easier to replace the collimators on the cameras 18 and 19.

Figures 2, 3, 6A, 6B:
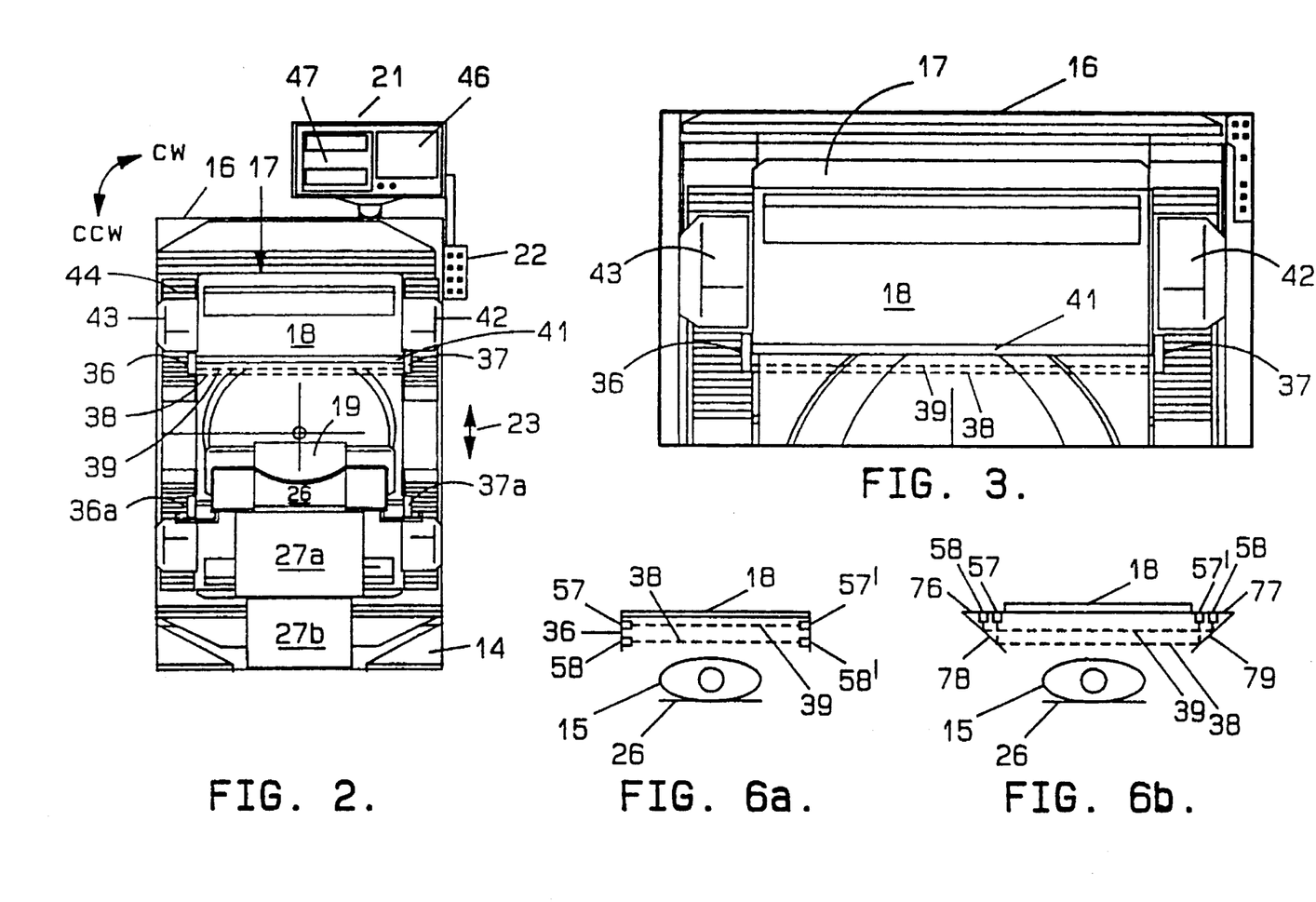

In FIG. 2, which is the front view of the system of FIG. 1, it is seen that both of the gamma cameras 18 and 19 have proximity controllers attached thereto. For example, gamma camera 18 has the proximity controllers 36 and 37 spaced apart so as to provide two parallel planes of energy beams separated from and spanning across the face of the collimator. The parallel planes of energy beams are indicated by the dashed lines 38 and 39. The dashed line 39 is closest to the collimator 41 associated with the camera 18. The camera 19 is also shown as having spaced apart proximity controllers 37a and 38a attached to the camera unit and slightly removed from the collimator so that energy beams traversing the space between the proximity controllers are slightly removed from the collimator.

The camera is attached to yoke arms within the box-like covers 42 and 43, respectively. The yoke arms are attached to a ball-screw type axles, not shown, within the rotor. When the in-out motor assigned to either of the cameras is operated, the balls-screw axles are rotated to,individually cause either of the cameras 18 or 19 or both to move closer together or further apart. It is the control of this in-out motion that is a major object of the invention described herein.

The screen of monitor 21 is divided into two sections. The first section 46 displays the image of the patient, the second section 47 indicates the motion of the cameras and the bed. This includes the in-out motion, the pivoting motion and the rotary of the cameras along with the longitudinal motion, the up and down motion and the pivoting motion around axis 33 of the bed. In addition, section 47 may relay instructions or messages for the operator.

The yoke arms of the camera extend into the interior of the rotor. The opening for the yoke arms are protected by dust covers such as the accordian-like dust cover indicated at 44.

A pressure sensitive device (PSD) 41 serves to stop any motion in the event it is actuated. This is a fall-safe protective device. The PSD could be set to actuate the individual motor to move the camera outward.

Under normal body scanning conditions, the camera is positioned so that the outer contour of the patient whose body is being imaged is between beams 38 and 39. This position is attained because the cameras normally are caused to travel inwardly when neither beam 38 or 39 is broken. When any of beams 38 are broken there is no in-out motion since the motor is not energized. When any of the beams 39 are broken, then the motor causes the in-out motion to be outward. Just as when the pressure sensitive plate 41 is actuated, the motor causes the cameras to move radially, outward away from the patient's body.

Figure 4:
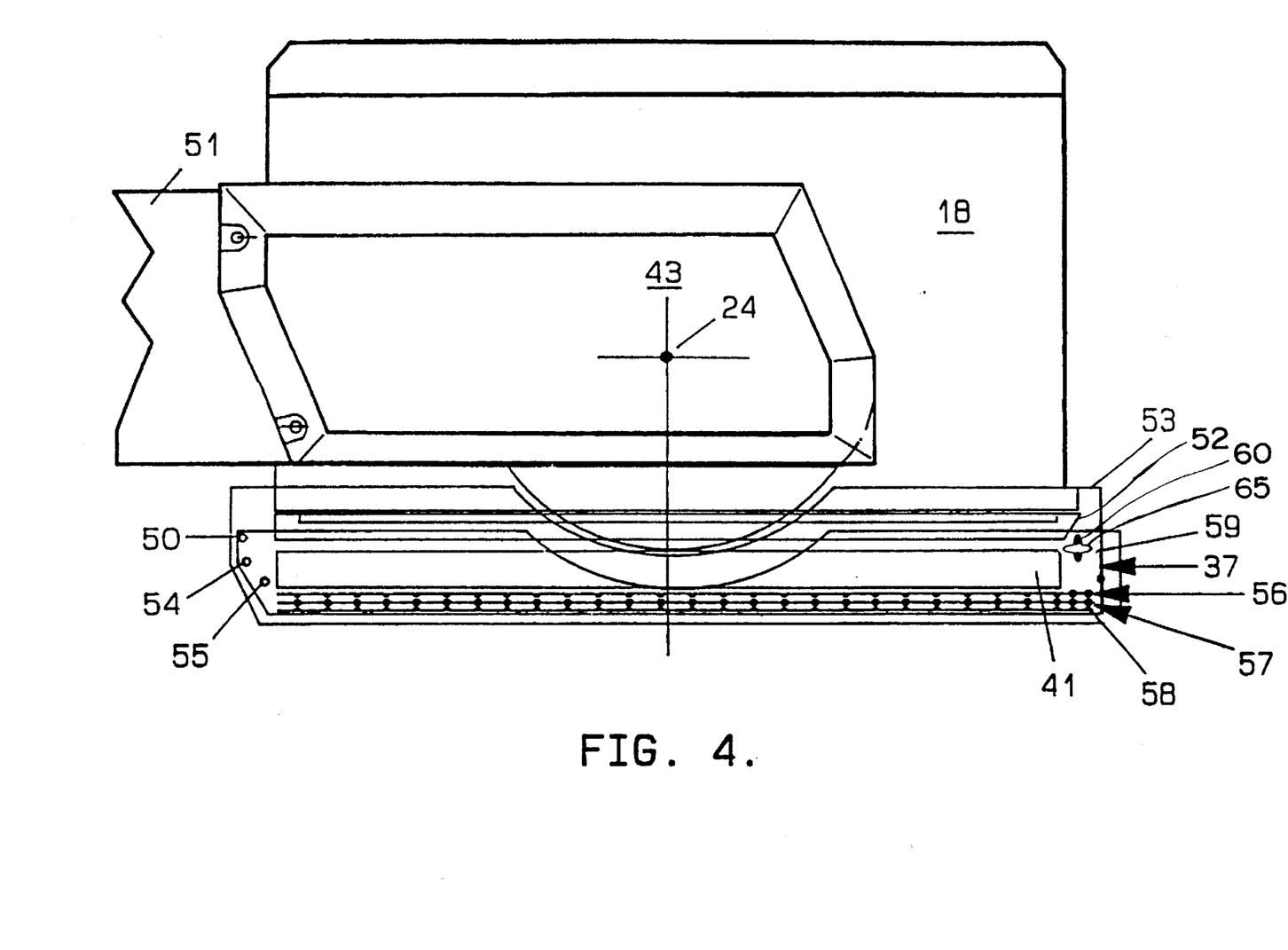
FIG. 4 is a side view of the gamma camera shown in FIG. 3 with one of the proximity controllers removed so that details of the other proximity controller are shown.

FIG. 4 shows details of the proximity control unit 37. It should be understood that one proximity control unit 36 may be an energy transmitting unit while the other proximity control unit such as unit 37 may be an energy receiving unit. Alternatively, each unit could comprise energy receivers and/or transmitters. For purposes of the explanation, in FIG. 4, unit 37 is considered an energy transmitting unit. FIG. 4 shows camera 18 mounted to the yoke arm 51 covered by yoke arm cover 43. The camera can be pivoted around pivot point 24 by a motor and controls not shown. The gamma camera 18 includes a plurality of photomultipliers, not shown, attached to a scintillating detecting crystal also not shown. When a photon of gamma energy strikes the detecting crystal, it scintillates. Photomultiplier tubes in the camera detect the scintillation and convert the scintillation into electrical energy. As is customary with all "Anger" type gamma cameras, the camera computes the location of the photon impingement of the crystal and the total energy.

A collimator unit 52 is shown mounted to the detecting or crystal side of the gamma camera. Also attached to the gamma camera is the proximity control unit 37. A flange-like cover 53 covers the proximity control unit, Shown as part of the proximity control unit 37 are multiple rows of energy transmitters such as light emitting diodes (LEDs). These rows are shown as rows 56, 57 and 58. The LEDs transmit energy in the form of infra-red light towards solid state light receivers on the oppositely disposed proximity control unit 36. While LEDs and solid state light receivers are indicated, the invention is sufficiently broad to cover other energy transmitters and receivers or other arrangements of the transmitters and receivers. For example, the transmitters and receivers could be on the same side with a reflector on the opposite side.

The multiple rows of transmitters and receivers are provided in order to accommodate different size collimators. When different size collimators are used, different pairs of the multiple rows are used. Thus, either rows 56 and 57 or rows 57 and 58 are used to provide the two parallel planes of energy beams between which the camera position is maintained during scan operations. More parallel rows could be provided to accommodate even other different size collimators. Also, the proximity units 36, 37 could be physically extended toward the patient when a larger collimator is used.

When a larger collimator is in place and the different rows are used to accommodate the larger size collimators, then rows 57 and 58 are energized. Then if the light emitted by the LEDs of row 58 encounter an object that is opaque to the light beams, such as the patient's body, the in-out motor will be de-energized and stop operating. When the light beams from LEDs in row 58 are not interrupted, then the motor is energized to bring the cameras closer together, that is closer to the patient's body. As soon as any of the beams from the LEDs of row 58 are interrupted, then the in-out motor is de-energized to stop the movement of the cameras. If the patient's body then breaks any of the beams from row 57, the in-out motor is actuated to separate the cameras, that is to move the cameras away from the patient. If the cameras are positioned such that the LEDs of row 57 are once again transmitting uninterruptedly to the receivers of the corresponding row 57 in proximity control unit 36, the motor is again de-energized. If the patient's body stops interfering with the light beams from the LEDs of row 58, then the in-out motor is actuated to bring the cameras closer together. In this manner, the cameras are kept in position so that the contour of the body is between rows 58 and 57.

The same type of operation occurs when the rows 56 and 57 are used; that is when a smaller collimator is in place. When a smaller collimator is used, the pressure sensitive device 41 is moved up higher. Then the energy transmitters of rows 56 and 57 both transmit beams of energy that normally impinge on energy receivers on proximity control unit 36 to control the in-out motor as explained. The transmitters and receivers are shown mounted on printed circuit boards, such as board 59 on which are mounted the rows 56, 57, 58 of energy transmitters.

An alternative mechanical arrangement for accommodating different sized collimators is also shown in FIG. 4. More particularly, slots such as slot 60 and fastener 65 to enable radially moving the proximity control units are illustrated.

The arcuate sections in the cover 53 and in the contour of the printed circuit board 59 are clearances used when the camera pivots around pivot point 24. The printed circuit board 59 holds the LEDs or the solid state light receivers of unit 36.

Also mounted on the printed circuit board 59 are a set of energy transmitters and oppositely disposed receivers that provide "early warning" energy beams. The early warning energy beams are used particularly during whole body scans where the patient is moved linearly and longitudinally relative to the camera. In a preferred embodiment, the patient bed 26 is moved longitudinally until the entire patient has gone past the camera or cameras. Then the scan is commenced by moving the camera toward the patient on the bed and moving the bed longitudinally past the cameras back to the starting point while the cameras detect the gamma radiation.

As the patient is moved back if any of the energy beams generated by any of the early warning energy transmitters 50, 54, or 55 is interrupted, the in-out motor is caused to move the camera or cameras away from the patient. The movement away continues until beams from row of detectors closest to the crystal are no longer interrupted or until a manual override, not shown, is operated to remove power from the in,out motor.

While early warning transmitters (and receivers) are shown only on one side of the camera, it should be understood that within the scope of the invention they could be mounted on the other side of the camera or on both sides of the camera.

Figure 5:
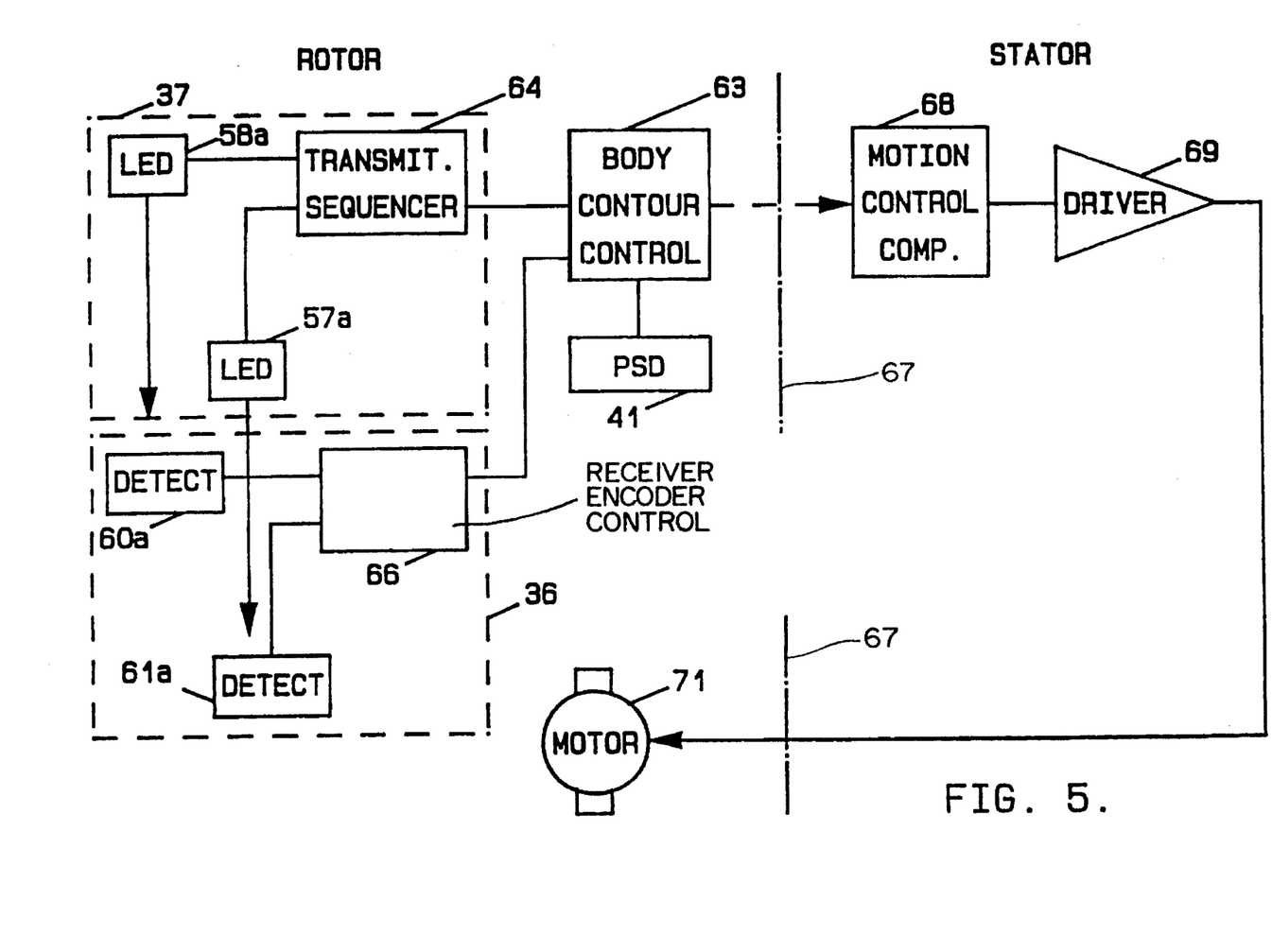
FIG. 5 is a block diagram showing of the controls for the inventive gamma camera system.

The block diagram of FIG. 5 show LEDs of rows 57 and 58, such as LED 58a and LED 57a. These LEDs operate to transmit energy preferably in the form of infra-red light to detectors, such as detectors 60a and 61a in corresponding rows on a proximity control unit 36. The transmission and receipt of the light energy is under the control of the body contour controller 63.

Means are provided to assure that the receivers operate only responsive to light from a transmitter to which the receiver is coupled. This arrangement prevents the operation of the motor responsive to reflected energy being received by a receiver not coupled to the transmitter: herein sometimes referred to as "cross-talk" more particularly, transmitter sequencer 64 causes the sequenced LED of the proper row to transmit while the receiver encoder 66 receives information only from the receiver coupled to the transmitting transmitter of the proximity control unit 37. The information from the body contour controller 63 is transmitted through slip rings indicated by the dashed lines 67 to the motion controlling computer 68. The motion controlling computer causes the motor driver 69 to energize the in-out motor, shown as motor 71, in the proper direction. The connection between the motor driver and the in-out motor 21 may also be through slip rings as indicated by the dashed line 67. The slip rings are used to couple power and commands between the stator and the rotor.

In practice, single pairs of transmitters and receivers are used at any one instant under the control of the sequencer 64 and encoder 66. The pairs are in effect "scanned" at a rate that enables all the pairs about 20 times per second. In a preferred embodiment, there are about 200 pairs. The scan time can be shortened by scanning two spaced apart pairs at the same time.

When the beam from an LED in row 58a to a detector in row 60a is broken, then power to the motor 71 is turned off. Prior to that, the motor is powered to cause the gamma camera to move closer to the patient. Upon breaking any of the beams extending from row 58 in unit 37 to row 60 in unit 36 the in-out motor 71 is de-energized and stops the movement of the gamma camera. Similarly, when any of the beams from the LEDs of row 57 such as LED 57a is broken on its way to the receivers of corresponding row 61, such as receiver 61a; in proximity control unit 36, then the motor 71 associated with the camera is powered to cause the gamma cameras to move in a direction away from the patient. If something is wrong with the operation so that breaking the beam from a LED of row 57 to a receiver of row 61 does not cause the cameras to move apart, then the body will press against pressure sensitive device 41 which will then stop all motion of the gamma cameras. That is, the signal from the body contour controller 63 to the motion control computer 68 can be derived from the receiver encoder 66 or from the pressure sensitive device 41.

The schematic showing of FIG. 6a is an embodiment wherein the proximity controllers are mounted extending in the direction of radial movement of the camera 18 toward the patient on bed 26. The proximity controller 36 includes, for example, a plurality of rows 57 and 58 of LEDs. The LEDs in a preferred embodiment transmit beams of infra-red light to similarly placed rows of infra-red light sensors 57 and 58. Thus, parallel spaced apart energy beams are produced.

FIG. 6b offers a variation of the embodiment of FIG. 6a. The rows of transmitters 57, 58 are mounted on a plate 76 extending transverse to the direction of radial motion of the camera 18 toward or away from the patient 15 on bed 26. The rows of receivers 57, 58 are also mounted on a plate 77 extending transverse to the radial motion. Reflecting surfaces 78 and 79 direct the energy beams 38 and 39 to span the front face of the camera in planes parallel to the detector face of the camera in the same manner that the energy beams 38 and 39 span the detecting face of the camera in FIG. 6a. It should be understood that within the scope of the invention the configuration of the transmitters and receivers could be combinations of the schematic showings of FIGS. 6a and 6b.

A system is thereby provided wherein the outer contour of the patient's body is maintained a fixed small distance away from the collimator of the gamma camera scanning the body whether the system operates when a whole body scan is being performed or when a computerized tomographic scan is being performed. In general, the system contains two well defined optical screens located Just above the detector of a gamma camera. The electronics associated with the optical screen are sensitive to any opaque disturbance of the energy screens. The energy screens are comprised of beams of energy such as light rays. Using the information from the optical energy screens, a command is sent to the in-out motor 71 in a way that minimizes the patient-detector distance to a few millimeters. The system comprises two electronic proximity control units attached to the detector side of the gamma camera. One of the units has a number of energy emitters and the other attached unit has a number of energy receivers. The emitters and receivers are arranged either oppositely disposed in two operating layers or disposed relative to reflecting surfaces with a small internal distance between them. In either configuration, the proximity controller, for example, yields light rays in parallel layers so that the system can maintain the outer contour of the patient's opaque body between the two parallel layers.

During a typical scan, the in-out motor moves the camera toward the patient when no disturbances are detected by the layered optical screens and it moves the camera away from the patient when inner layer is disturbed. The camera is not moved in an in or out direction when outer layer is disturbed and the inner layer is not disturbed. The in or out motion does not interfere with the scan motion; i.e., with the rotational motion for ECT scans and linear longitudinal motion for whole body scans.

Among other things, the unique proximity controller enables the gamma camera to be as close as possible to the patient during the entire scan. Thus, for ECT scans, for example, the camera is even closer to the patient on the average than the proximity achieved with elliptical scans. In addition, the unique proximity controllers dramatically speed up the throughput of the system since the time consuming preliminary scan loci learning or testing cycles of the prior art are no longer necessary.

Having thus described the invention with particular reference to the preferred forms thereof, it will be obvious to those skilled in the art to which the invention pertains after understanding the invention that various changes and modifications may be made therein without departing from the spirit and scope of the invention as defined by the claims appended hereto.

What is claimed is:

1. A gamma camera system comprising:

a gantry having at least one gamma camera mounted thereon for use in performing scans of a patient, controls for minimizing the distance between the patient and the gamma camera during said scans, said controls limited to a first proximity control for providing a first energy screen of multiple energy beams at a first distance from the detector of the gamma camera and a second proximity control for providing a second energy screen of multiple energy beams at a second distance from the detector of the gamma camera, said second distance being larger than said first distance, said controls minimizing the distance between the gamma camera and the patient's body by controlling the movements of the gamma camera to maintain the contour of the patient's body between said first and second energy screens, said multiple energy beams being comprised of a number of beams sufficiently close to each other so that cross-talk may occur between individual transmitters and receivers that are not oppositely disposed, and a cross-talk avoidance arrangement for avoiding cross-talk between individual receivers and transmitters that are not oppositely disposed.

2. The gamma camera system of claim 1 wherein a transmitting line of more than five energy transmitters are provided for transmitting said energy beams for each of said energy screens, and a receiving line of more than five energy receivers are provided for receiving said beams for each of said energy screens, said transmitting lines and said receiving lines being spaced apart on opposite sides of the detector and parallel thereto at said first distance and said second distance.

3. The gamma camera system of claim 2 wherein said energy transmitters comprise light emitting diodes and said energy receivers comprise light sensitive detectors.

4. The gamma camera system of claim 2 wherein said energy transmitters comprise infra-red emitting diodes and said energy receivers comprise infra-red sensitive detectors.

5. The gamma camera system of claim 2 including a fall-safe arrangement for ensuring that the camera does not injure the patient.

6. The gamma camera system of claim 5 wherein said fail-safe arrangement comprises a pressure-sensitive device mounted and connected to cause said camera to move away from said patient when said pressure-sensitive device is actuated.

7. The gamma camera system of claim 5 wherein said fail-safe arrangement comprises a pressure-sensitive device mounted and arranged to cause said camera to stop all movement when said pressure-sensitive device is actuated.

8. The gamma camera system of claim 2 wherein each of said first and second screens of energy comprise a series of energy beams optical controls, said camera including a radiation detecting side, said optical controls comprising:

a first series of energy:transmitters each mounted a first distance away from the radiation detecting side of said gamma camera, a first series of energy receivers each mounted oppositely disposed from said first series of energy transmitters at said first distance away from the radiation detecting side of said gamma camera so that energy transmitted from said first series of energy transmitters impinge on said first series of energy receivers after spanning the detecting side of the camera, a motor, said motor operated responsive to an interruption of transmitted energy going from said first series of transmitters to said first series of receivers to move said camera radially away from the patient, a second series of energy transmitters each mounted a second distance away from the radiation detecting side of the camera, a second series of energy receivers mounted oppositely disposed from said second series of energy transmitters and at said second distance away from said detector of said camera so that energy transmitted from said second series of energy transmitters impinge on said second series of energy receivers after spanning the detecting side of the camera, means for inhibiting the operation of said motor responsive to interference with the energy transmitted by said second series of energy transmitters toward the second series of energy receivers while there is no interference with the energy transmitted by the first series of energy-transmitters toward the first series of receivers, and controls for operating said motor to move said camera towards said patient when there is no interference with the energy extending from the first series of transmitters to the first series of receivers and with the energy extending from the second series of transmitters to the second series of receivers.

9. The gamma camera system of claim 1 wherein said first proximity control consists of a first line of a first plurality of energy transmitters mounted on said gamma camera at said first distance and a first line of a first plurality of energy receivers also mounted on said gamma camera at said first distance and on opposite sides of the detector to provide said first energy screen, wherein said second proximity control consists of a second line of a second plurality of energy transmitters and a second line of a second plurality of energy receivers both mounted on said gamma camera at said second distance at opposite sides of said detector whereby two parallel energy screens are provided spaced apart from each other and parallel to the detector, wherein said energy screens comprise individual beams of energy transmitted from the lines of energy transmitters at one side of the detector facing towards the lines of energy receivers at the other side of the detector.

10. The gamma camera system of claim 9 wherein said gantry is equipped with a radial drive, said radial drive radially moving the gamma camera toward said patient when neither said first screen of energy nor said second screen of energy is interrupted.

11. The gamma camera system of claim 10 wherein a radial movement brake device is provided for stopping the radial movement of the gamma camera when said first energy screen is interrupted while said second energy screen is not interrupted.

12. The gamma camera system of claim 11 wherein said first and second proximity controls are connected to cause said radial drive to move said gamma camera radially away from said patient when said first and second energy screens are both interrupted.

13. The gamma camera system of claim 12 wherein a plurality of gamma cameras are mounted on said gantry for use in performing scans of the patient, said radial drive comprising a motor individually associated with each of the plurality of gamma cameras for individually moving each of said gamma cameras radially relative to said patient.

14. The gamma camera system of claim 10 wherein said cross-talk avoidance arrangement comprises circuitry for energizing the transmitters and receivers in pairs so that the energy from the transmitters are transmitted in a manner such that energy can be received by only one receiver at a time.

15. The gamma camera system of claim 14 wherein the transmitters and corresponding receivers of the pairs are energized serially, one pair at a time.

16. The gamma camera system of claim 1 wherein said gamma camera includes a collimator, and wherein the proximity controls changes the minimum distance between patient and the gamma camera during said scans when different size collimators are used.

17. The gamma camera system of claim 16 wherein when different size collimators are used then multiple lines of energy transmitters at one side of camera and multiple lines of energy receivers at the other side of the gamma camera are used, and     switching circuitry for causing different pairs of said multiple lines of transmitters and receivers to be used depending on the size of the collimator used.

18. The gamma camera system of claim 16 including a mechanical actuator for mechanically moving said proximity controls to accommodate said different size collimators.

19. The gamma camera system of claim 1 wherein an early warning system is provided to prevent said camera from moving toward said patient when said early warning system is actuated by the body of the patient as the camera is being moved laterally toward said patient.

20. The gamma camera system of claim 19 wherein said early warning system comprises:

at least a third screen of energy beams perpendicular to said first and said second energy screens said third screen being at the side of the gamma camera moving towards said patient, and     a drive responsive to interruption of said third screen for moving said gamma: camera away from said patient in a direction normal to said third screen.

21. The gamma camera system of claim 20 wherein said third screen is provided by transmitters and receivers mounted spaced apart opposite each other on a side of said gamma camera.

22. A method of controlling the proximity of the gamma camera to a patient during a scan of the patient, said method comprising the steps of:

spanning the detector side of the gamma camera with only first and second energy screens each comprised of individual beams of light energy, each energy screen comprising a plurality of light beams,     transmitting each of said light beams individually using a plurality of light transmitters,     detecting each of said light beams individually using a plurality of light detectors,     locating said first and second screens at a first and second distance respectively from the detector of the gamma camera, said first distance being smaller than said second distance,     providing said individual light beams sufficiently close to each other so that cross-talk may occur between individual transmitters and receivers that are not oppositely disposed,     avoiding cross-talk between transmitters and receivers that are not oppositely disposed,     moving said gamma camera radially towards the patient when there is no interference with either said first or second energy screen,     moving said gamma camera radially away from said patient when there is interference with both said first and said second energy screens, and     inhibiting the radial movement of said gamma camera at all times that there is no interference with said first energy screen while there is interference with said second energy screen.

* * * * *